(12) United States Patent
Ben-Ezer

(10) Patent No.: US 8,475,006 B2
(45) Date of Patent: Jul. 2, 2013

(54) DARK FIELD ILLUMINATOR AND A DARK FIELD ILLUMINATION METHOD

(75) Inventor: Zehava Ben-Ezer, Moshav Balfouria (IL)

(73) Assignee: Camtek Ltd., Migdal Ha'emek (IL)

( * ) Notice: Subject to any disclaimer, the term of this patent is extended or adjusted under 35 U.S.C. 154(b) by 897 days.

(21) Appl. No.: 12/375,554

(22) PCT Filed: Aug. 1, 2007

(86) PCT No.: PCT/IL2007/000962
§ 371 (c)(1),
(2), (4) Date: Nov. 17, 2009

(87) PCT Pub. No.: WO2008/015677
PCT Pub. Date: Feb. 7, 2008

(65) Prior Publication Data
US 2010/0073935 A1    Mar. 25, 2010

Related U.S. Application Data

(60) Provisional application No. 60/821,203, filed on Aug. 2, 2006.

(51) Int. Cl.
*F21V 7/00*    (2006.01)

(52) U.S. Cl.
USPC ...... 362/296.01; 362/297; 362/298; 362/299; 362/302; 362/304

(58) Field of Classification Search
USPC ............................................. 362/296.01–305
See application file for complete search history.

(56) References Cited

U.S. PATENT DOCUMENTS

| | | | | |
|---|---|---|---|---|
| 4,626,079 | A * | 12/1986 | Nakamura et al. | 359/387 |
| 6,219,476 | B1 | 4/2001 | Kususawa et al. | |
| 2003/0030803 | A1* | 2/2003 | Kusuzawa | 356/336 |

OTHER PUBLICATIONS

International Search Report for International Application No. PCT/IL07/00962 mailed Sep. 26, 2008.

* cited by examiner

*Primary Examiner* — Sean Gramling
(74) *Attorney, Agent, or Firm* — Oren Reches

(57) ABSTRACT

A dark field illuminator that includes: (i) a light source adapted to provide ring of light characterized by uniform intensity distribution; (ii) a collimating ring adapted to receive the ring of light and to direct collimated light beams towards an area of an inspected object such that different points within the area are illuminated by identical cones of light characterized by an incidence angle; and wherein the collimating ring and the light source are co-centric to an optical axis of the dark field illuminator.

24 Claims, 12 Drawing Sheets

103

> Providing, by a light source and to a collimating ring, a ring of light that is characterized by uniform intensity distribution. 211

> Directing, by the collimating ring, a collimated ring of light towards an area of an inspected object such that different points within the area are illuminated by identical cones of light, the cones of light are characterized by an incidence angle. The collimating ring and the light source are co-centric to an optical axis of a dark field illuminator that includes the light source and the collimating ring. 221

Directing, by a ring reflector and towards a collimating ring, reflected ring of light characterized by a uniform intensity distribution. 212

Directing, by the collimating ring, a collimated ring of light towards an area of an inspected object such that different points within the area are illuminated by identical cones of light characterized by an incidence angle. Wherein the collimating ring, the ring reflector and the light source are co-centric to an optical axis of a dark field illuminator that include the light source and the collimating ring. 222

Three dimensional view

103

DARK FIELD ILLUMINATOR AND A DARK FIELD ILLUMINATION METHOD

CROSS-REFERENCE TO RELATED APPLICATIONS

This patent application is a National Phase Application of PCT International Application No. PCT/IL2007/000962, entitled "DARK FIELD ILLUMINATOR AND A DARK FIELD ILLUMINATION METHOD", International Filing Date Aug. 1, 2007, published on Feb. 7, 2008 as International Publication No. WO 2008/015677, which in turn claims priority from U.S. Provisional Patent Application No. 60/821,203, filed Aug. 2, 2006, both of which are incorporated herein by reference in their entirety.

RELATED APPLICATIONS

This patent application claims priority from U.S. provisional application Ser. No. 60/821,203 filing date 2 Aug. 2006.

FIELD OF THE INVENTION

The invention relates to a dark field illuminator and to a dark field illumination method, especially in optical inspection systems that inspect electrical circuits.

BACKGROUND OF THE INVENTION

Illuminating an object in machine-vision application needs to be performed in a uniform manner over a field of view (FOV). This includes the illumination intensity and angular incidence impinging at each and every point in the FOV.

Bright field illumination (sometimes called vertical illumination or coaxial illumination) can be made uniform, with an example of a reflected Kohler illumination in a microscope working through a telecentric objective lens.

Dark field illumination of an integrating sphere can make a uniform illumination over the FOV, but is very inefficient.

There is a growing need to provide efficient dark field illuminator and methods for dark field illumination.

SUMMARY OF THE INVENTION

A dark field illuminator, including: a light source adapted to provide a ring of light characterized by uniform intensity distribution; a collimating ring adapted to receive the ring of light and to direct collimated light beams towards an area of an inspected object such that different points within the area are illuminated by light beams that form substantially identical cones of light; and wherein the collimating ring and the light source are co-centric to an optical axis of the dark field illuminator.

A dark field illuminator, including: a light source adapted to provide a ring of light characterized by uniform intensity distribution; a folding ring reflector adapted to receive the ring of light and to direct reflected light beams towards a collimating ring; a collimating ring adapted to receive the reflected light beams and to direct collimated light beams towards an area of an inspected object such that different points within the area are illuminated by identical cones of light; wherein the collimating ring, the ring reflector and the light source are co-centric to an optical axis of the dark field illuminator.

A dark field illuminator, including: a light source adapted to provide ring of light characterized by uniform intensity distribution; a folding ring reflector adapted to receive the ring of light and to: direct first reflected light beams towards an area of an inspected object, direct second reflected light beams towards a refracting ring, and direct third reflected light beams towards an oriented ring reflector; wherein the first reflected light beams illuminate different points within area by substantially identical cones of light characterized by a first incidence angle; wherein the refracting ring alters an angle of incidence of the second reflected light beams such as to illuminate the different points by substantially identical cones of light characterized by a second incidence angle; wherein the oriented ring reflector reflects the third reflected light beams such as to illuminate the different points by substantially identical cones of light characterized by a third incidence angle; wherein the folding ring reflector, the oriented ring reflector and the refracting ring are co-centric to an optical axis of the dark field illuminator.

A dark field illuminator, including: a light source adapted to provide ring of light characterized by uniform intensity distribution; multiple refracting rings; a reflector ring positioning unit, adapted to position a folding ring reflector at a selected position out of multiple possible positions; wherein when the folding ring reflector is positioned in a selected position it directs a reflected light beams towards a selected refracting ring out of the multiple reflecting rings; wherein a selected refracting ring alters an angle of incidence of the reflected light beams such as to illuminate different points within an area of an inspected object by substantially identical cones of light characterized by an incidence angle; wherein different refracting rings are associated with different incidence angles; and wherein the folding ring reflector, each ring refractor and the light are co-centric to an optical axis of the dark field illuminator.

A dark field illumination method, including: providing, by a light source and to a collimating ring, ring of light that are characterized by uniform intensity distribution; directing, by the collimating ring, collimated light beams towards an area of an inspected object such that different points within the area are illuminated by identical cones of light; wherein the collimating ring and the light source are co-centric to an optical axis of a dark field illuminator that includes the light source and the collimating ring.

A dark field illumination method, including: directing, by a ring reflector and towards a collimating ring, a reflected ring of light characterized by a uniform intensity distribution; directing, by the collimating ring, collimated light beams towards an area of the inspected object such that different points of within the area are illuminated by identical cones of light characterized by an incidence angle; wherein the collimating ring, the ring reflector and the light source are co-centric to an optical axis of a dark field illuminator that includes the light source and the collimating ring.

A dark field illumination method, including: illuminating a folding ring reflector by ring of light characterized by a uniform intensity distribution; directing, by the folding ring reflector, first reflected light beams towards an area of an inspected object such as different points within the area are illuminated by substantially identical cones of light characterized by a first incidence angle; directing, by the folding ring reflector, second reflected light beams towards a refracting ring; directing, by the folding ring reflector, third reflected light beams towards an oriented ring reflector; altering, by the refracting ring, an angle of incidence of the second reflected light beams such as to illuminate the different points by substantially identical cones of light characterized by a second incidence angle; and reflecting, by the oriented ring reflector the third reflected light beams such as to illuminate the different points by substantially identical cones of light characterized by a third incidence angle; wherein the ring reflector, the oriented ring reflector and the refracting ring are co-centric to an optical axis of a dark field illuminator that includes the light source, the folding ring reflector, the oriented ring reflector and the refracting ring.

A dark field illumination method, including: positioning a folding ring reflector at a selected position out of multiple possible positions; directing reflected ring of light characterized by uniform intensity distribution towards a selected refracting rings out of a group of refracting rings; altering an angle of incidence of the reflected ring of light such as to illuminate different points within an area of an inspected object by substantially identical cones of light characterized by an incidence angle; wherein different refracting rings are associated with different incidence angles; wherein the folding ring reflector, each ring refractor and the light are co-centric to an optical axis of a dark field illuminator that includes the light source and the group of refracting ring.

BRIEF DESCRIPTION OF THE DRAWINGS

The present invention will be understood and appreciated more fully from the following detailed description taken in conjunction with the drawings in which:

FIGS. 1A-8A are cross sectional views of dark field inspection systems, according to various embodiments of the invention;

FIG. 1B, 2B, 3B and 8B are flow charts illustrating dark field illumination methods, according to various embodiments of the invention.

DETAILED DESCRIPTION OF THE DRAWINGS

The term "cone" (or "conic envelope") refers to the locus of all line segments joining a perimeter of an imaginary circular base to a point (also known as apex or vertex) lying off the plane of the imaginary circular base.

According to an embodiment of the invention each point within an area of an illuminated object is illuminated by a cone of light, while each point is the apex of the cone. The cone is defined by a zenith angle that is determined by the optical configuration of the dark field illuminator. Accordingly, each point is not illuminated by light beams that have an incidence angle that differs from that zenith angle.

The term "ring of light" refers to a three dimensional illumination pattern that has a ring shaped cross section. The cross section is taken along an imaginary plane that is traverse to a direction of propagation of the ring of light.

Various embodiments of the invention are herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

The dark field illuminator and method can be used for inspecting electrical circuits such as but not limited to wafers, printed circuit boards and the like.

The dark field illumination is substantially uniform both in intensity and in its angular incidence over relatively large field of view. The dark field illuminator can be used for machine vision applications and especially for automatic optical inspection of semiconductor wafers.

Although the following explanations refer to inspection that is based upon reflected light it is noted that the dark field illuminator and dark field inspection system can be configured for inspection of transparent or semi-transparent objects. Accordingly "reflected" and "transmissive" dark field inspection modes can be used. Those of skill in the art will appreciate that in "transmissive" mode the imaging optics and the dark field illuminator are located at opposing sides of the inspected object.

Figure 1A:
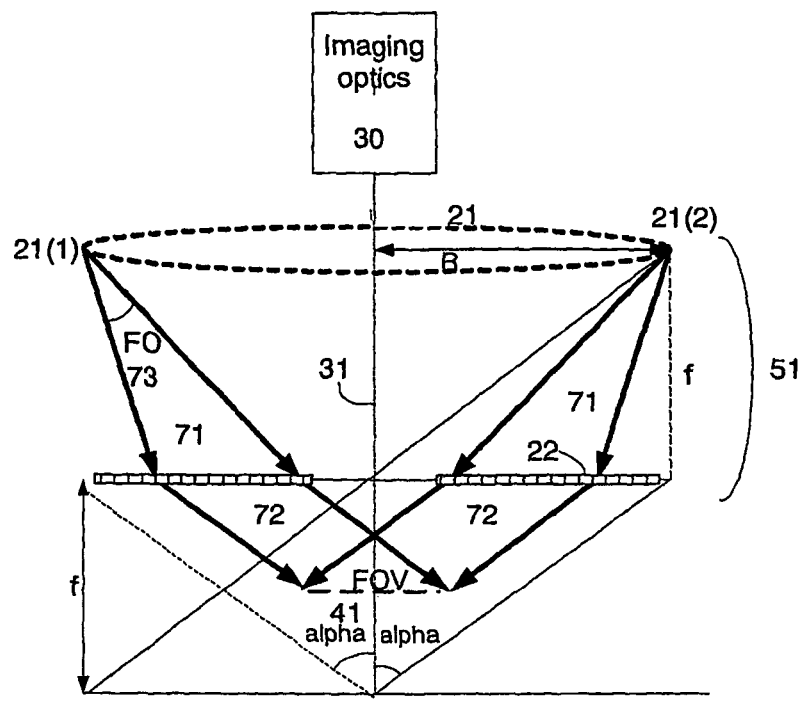
Figure 2A:
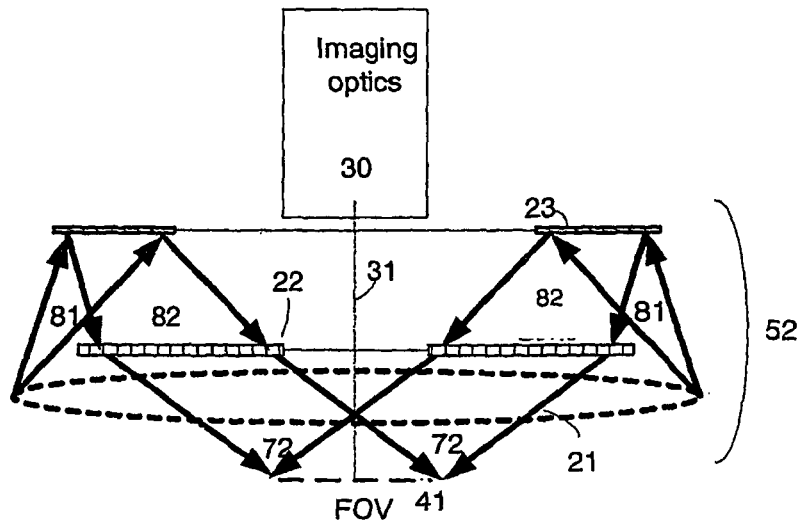
Figure 1C:
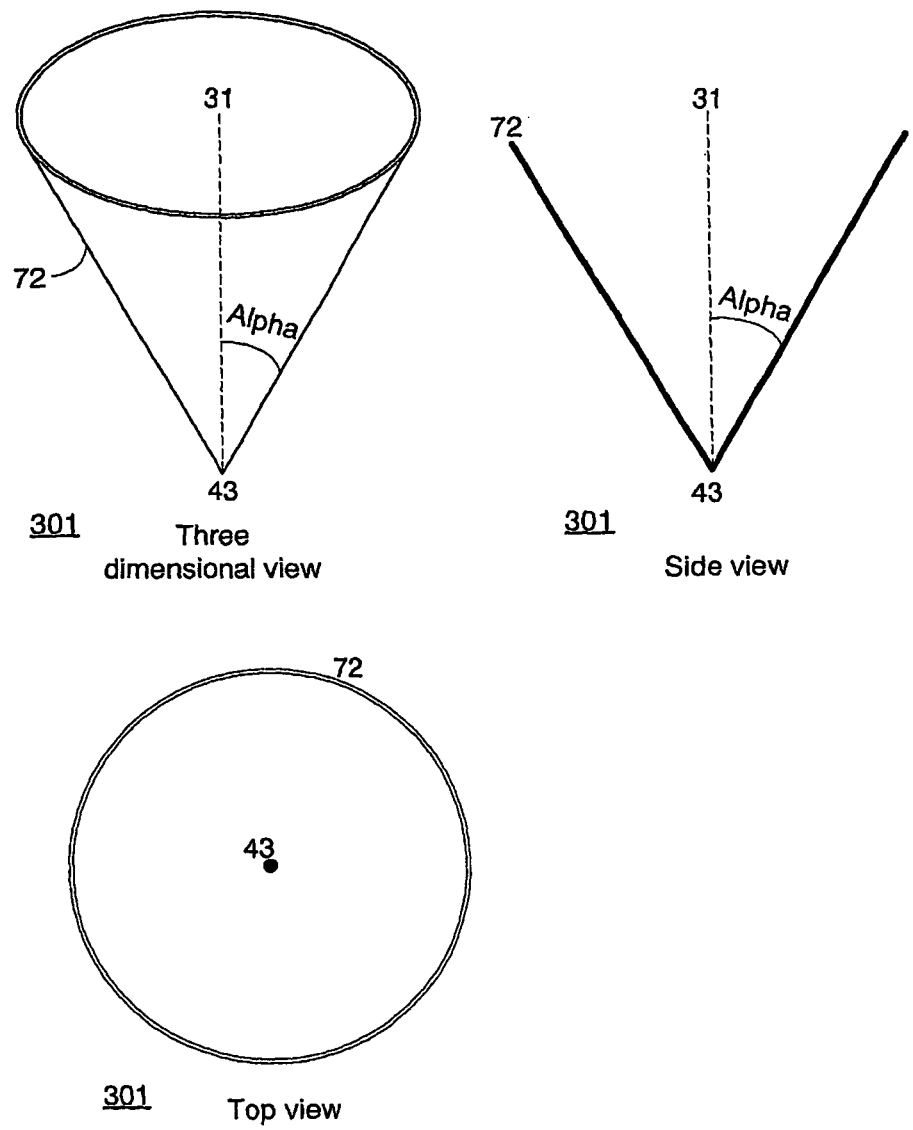
FIGS. 1C and 2C illustrate illumination patterns according to various embodiments of the invention.
Figure 2C:
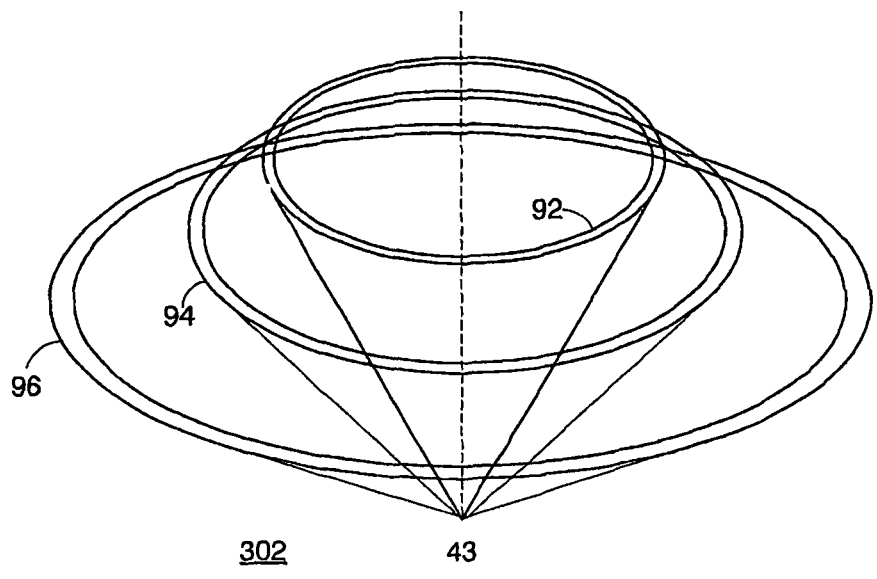
Figure 2C:
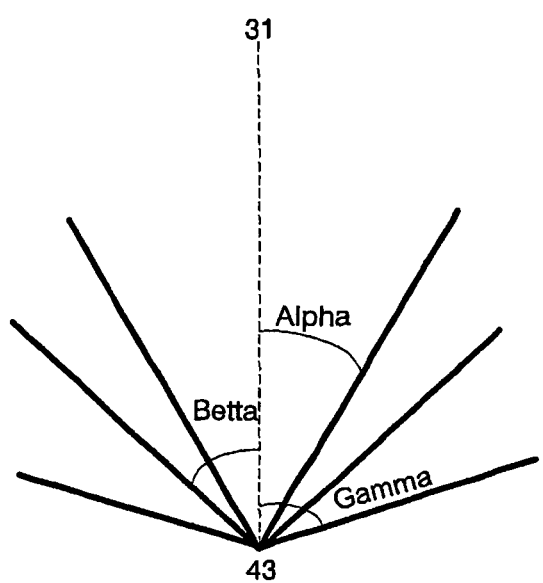

For simplicity of explanation the following illustrations FIGS. 1 and 2 include cross sections of various components (such as collimating lens 22) and a three dimensional representations of light source (denoted "ring light") 21.

For simplicity of explanation the illumination patterns of points within an area of an inspected object are represented by a spherical coordinate system. The optical axis of the dark field illuminator is the Z-axis and the incidence angles are zenith angles.

First Configuration

FIG. 1A is a cross sectional view of dark field inspection system 101 according to an embodiment of the invention.

Dark field inspection system 101 includes imaging optics 30 and dark field illuminator 51.

Dark field illuminator 51 includes collimating ring 22 (which is a collimating lens that has an annular shape) and a ring shaped light source 22. Collimating ring 22 and light source 21 are co-centric (co-centered) to an optical axis 31 of dark field illuminator 51.

Conveniently, collimating ring 22 and light source 21 are horizontal.

Light source 21 is illustrated as a dashed ring having radius R. It directs (towards collimating ring 22) ring of light 71 that is characterized by a uniform intensity distribution towards collimating ring 22. Ring of light 73 is bounded by two co-centric cones that have the same imaginary base (defined by light source 21) but spaced apart apexes. The cross section of these beams, taken along an imaginary plane that is parallel to optical axis 31 (and as illustrated in FIG. 1) is a fan. FIG. 1 illustrates two opposing points of light 21(1) and 21(2) that belong to light source 21. Light beams that define a fan of light are emitted from each point of 21(1) and 21(2) to be directed towards collimating ring 22. The fan opening (denoted FO) 73 is determined such that the ring of light illuminates at least a substantial portion of collimating ring 22, without directly impinging onto area 41.

Light source 21 can be a continuous light source. It can include a ring light fiber that is connected to a continuous source, such as a Tungsten-Halogen lamp. Light source 21 can be a pulsed light source. It can include a flash lamp.

Collimating ring 22 receives ring of light 71 and directs collimated light beams 72 towards an area (denoted Field Of View) 41 of an inspected object such that different points within area 41 are illuminated by light beams that form substantially identical cones of light.

The value of the zenith angle (of each of these cones) is responsive to the relationship between the focal length of collimating ring 22 (denoted f) and the radius (denoted R) of light source 21.

Conveniently, light source 21 is located at a back focal plane of collimating ring 22.

According to an embodiment of the invention imaging optics 30 can be lowered towards area 41, and especially lowered such that at least one lens of the imaging optics 30 (at least the lowest lens of imaging optics 30) is closer to area 41 than light source 21. This can be achieved by utilizing a light source that has an opening that is large enough to enable a lower portion of imaging optics 30 to enter through.

Conveniently, imaging optics 30 can be lowered as long as it does not block collimated light beams 72.

Collimating ring 22 can have an opening that is large enough to enable a lower portion of imaging optics 30 to enter through.

FIG. 1B is a flow chart of method 201 for dark field illumination, according to an embodiment of the invention.

Method 201 starts by stage 211 of providing, by a light source and to a collimating ring, a ring of light that is characterized by a substantial uniform intensity distribution. The ring of light includes light beams that are bounded by two co-centric cones that have the same imaginary base (defined by light source 21) but spaced apart apexes.

Referring to the example set fourth in FIG. 1A, light source 21 can direct ring of light 71 towards collimating ring 22.

Stage 211 is followed by stage 221 of directing, by the collimating ring, collimated light beams towards an area of an inspected object such that different points within the area are illuminated by substantially identical cones of light. The collimating ring and the light source are co-centric to an optical axis of a dark field illuminator that includes the light source and the collimating ring.

Referring to the example set fourth in FIG. 1A, collimating ring 22 directs collimated light beams 72 towards area 41.

It is noted that stage 221 can be followed by generating detection signals in response to light omitted from area 41, processing the detection signals to locate defects, and the like.

FIG. 1C illustrates illumination pattern 301, according to an embodiment of the invention.

Substantially each point of area 41 (such as arbitrary point 43) is illuminated by the same illumination pattern—illumination pattern 301. Illumination pattern 301 has a shape of a cone that is defined by zenith angle alpha. Illumination pattern 301 defines a conic surface where arbitrary point 43 is the apex.

Second Configuration

According to another embodiment of the invention a compact and folded dark field illuminator is provided. In this configuration a light source is inverted and directs the ring of light upward, towards a folding ring reflector (also referred to as top mirror). The folding ring reflector directs reflected light beams (also referred to as illumination cone) downward, towards the collimating ring.

FIG. 2A is a cross sectional view of dark field inspection system 102 according to another embodiment of the invention.

Dark field inspection system 102 includes imaging optics 30 and dark field illuminator 52.

Dark field illuminator 52 includes collimating ring 22, light source 21 and folding ring reflector 23. Folding ring reflector 23, collimating ring 22 and light source 21 are co-centric to the optical axis 31 of dark field illuminator 52. Conveniently, these components are horizontal.

Collimating ring 22 and light source are placed below folding ring reflector 23.

Light source 21 directs ring of light 81 towards ring reflector 23. Ring of light 81 is characterized by a uniform intensity distribution. Ring of light 81 is defined by light beams that are bounded by two co-centric cones that have the same imaginary base (defined by light source 21) but spaced apart apexes.

Folding ring reflector 23 is adapted to receive ring of light 81 and to direct reflected ring of light 82 towards collimating ring 22.

Collimating ring 22 is adapted to receive reflected ring of light 82 and to direct collimated ring of light 82 towards area 41 of an inspected object such that different points within the area are illuminated by identical cones of light.

Conveniently, the distance between folding ring reflector 23 and light source 21 is smaller than a focal length (f) of collimating ring 22.

FIG. 2B is a flow chart of method 202 for dark field illumination, according to an embodiment of the invention.

Method 202 starts by stage 212 of directing, by a folding ring reflector and towards a collimating ring, reflected ring of light that is characterized by a uniform intensity distribution. The reflected ring of light includes light beams that are bounded by two co-centric cones that have the same imaginary base but spaced apart apexes.

Referring to the example set fourth in FIG. 2A, folding ring reflector 23 receives ring of light 81 (from light source 21) and reflects the ring of light to provide reflected ring of light 82. Reflected ring of light 82 is directed towards collimating ring 22.

Stage 212 is followed by stage 222 of directing, by the collimating ring, collimated light beams towards an area of an inspected object such that different points within the area are illuminated by identical cones of light. Wherein the collimating ring, the folding ring reflector and the light source are co-centric to an optical axis of a dark field illuminator that includes the light source, the folding ring reflector and the collimating ring. The collimating ring and the light source are placed below the folding ring reflector.

Referring to the example set fourth in FIG. 2A, collimating ring 22 directs collimated light beams 72 towards area 41.

Exemplary illumination patterns of system 102 are illustrated in FIG. 1C.

It is noted that the dark field illuminators 51 and 52 of FIGS. 1A and 1B illuminate the whole area (the whole Field Of View) uniformly and with the same zenith angle (alpha) at each point in the FOV. Light source 21 is continuous over its perimeter, thus achieving radial symmetry of the illumination around the optical axis at each point in the FOV.

Third Configuration

According to further embodiments of the invention the collimating ring is replaced by multiple non-collimating rings such as refracting rings, and additionally or alternatively, by oriented reflecting rings.

A folding reflector ring directs a ring of light having a uniform intensity distribution, towards the non-collimating rings and can also direct light beams towards an area of an inspected object. The non-collimating rings direct light beams towards the area. Thus, each point within the area is illuminated by multiple cones, each cone defined by its own zenith angle, with only a very small angle of incidence variation over the illuminated area.

Figure 3A:
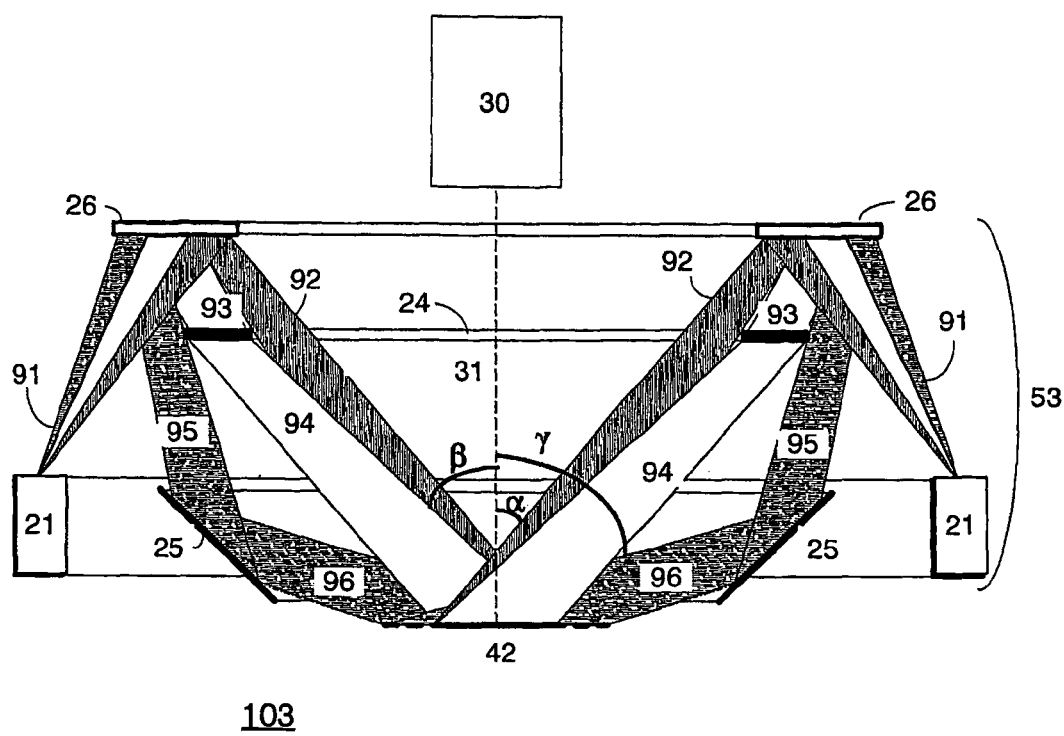

FIG. 3A is a cross sectional view of dark field inspection system 103 according to another embodiment of the invention.

Dark field inspection system 103 includes imaging optics 30 and dark field illuminator 53.

Dark field illuminator 53 includes: light source 21, folding ring reflector 26, refracting ring 24 and oriented ring reflector 25. Oriented ring reflector 25 is shaped as a truncated cone.

Light source 21, folding ring reflector 26, oriented ring reflector 25 and refracting ring 24 are co-centric to optical axis 31 of dark field illuminator 53. Refracting ring 24 and folding ring reflector 26 are located below folding ring reflector 26.

Light source 21 is adapted to provide ring of light 91 that is characterized by uniform intensity distribution. Ring of light 91 is bounded by two co-centric cones that have the same imaginary base but spaced apart apexes.

Folding ring reflector 26 is adapted to receive ring of light 91 and: (i) direct first reflected light beams (also referred to as internal portion of light) 92 towards area 42 of an inspected object, (ii) direct second reflected light beams (also referred to as middle portion of light) 93 towards refracting ring 24, and (iii) direct third reflected light beams (also referred to as external portion of light) 95 towards oriented ring reflector 25.

Each of first reflected light beams 92, second reflected light beams 93 and third reflected light beams 95 is circularly symmetric and is characterized by a uniform intensity distribution.

First reflected light beams 92 illuminate different points within illuminated area 42 by substantially identical cones of light, each characterized by a central zenith angle denoted alpha ($\alpha$).

Refracting ring 24 alters an angle of incidence of the second reflected light beams 93 to provide light beams 94 that illuminate the different points of area 42 by substantially identical cones of light characterized by a central zenith angle denoted betta ($\beta$). Refracting ring 24 can be a Fresnel lens and especially an annular portion of a circular Fresnel lens.

Oriented ring reflector (also referred to as bottom cone mirror) 25 reflects the third reflected light beams 95 such as to provide light beams 96 that illuminate the different points by substantially identical cones of light characterized by a central zenith angle denoted gamma ($\gamma$).

It is noted that folding ring reflector 26 effectively minimizes the ratio between: (i) the distance between the light source and the illuminated object, and (ii) the area size (the field of view).

Conveniently, alpha ($\alpha$) is smaller than betta ($\beta$) while betta ($\beta$) is smaller than gamma ($\gamma$). Gamma ($\gamma$) is very large and can be almost ninety degrees.

It is noted that dark field illuminator 53 can include multiple refracting rings (each associated with a different incidence angle), and additionally or alternatively, multiple oriented ring reflectors (each associated with a different incidence angle).

Figure 4A:
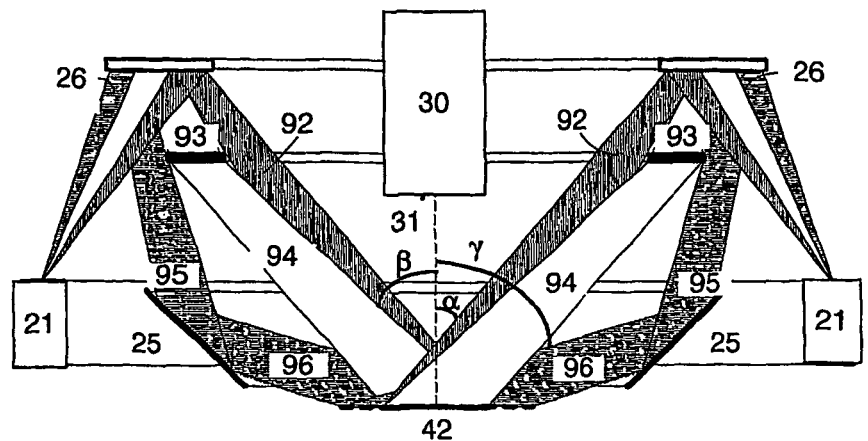
Figure 5A:
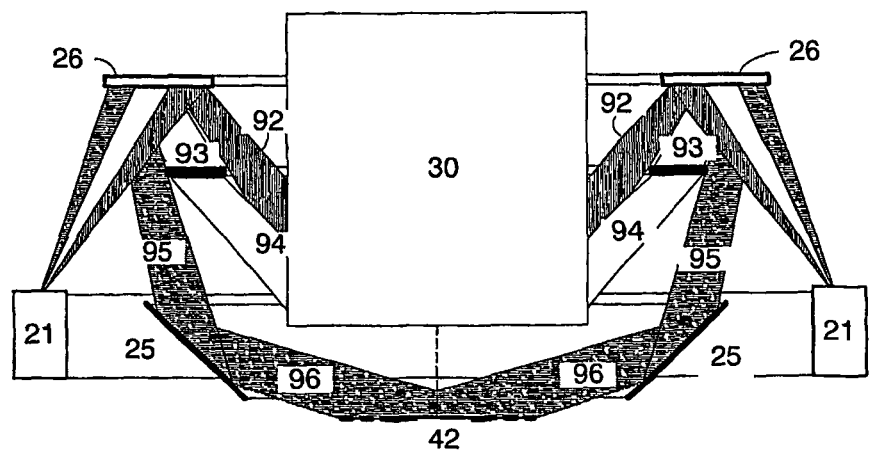

Dark field illuminator 53 has a cylindrical free space at its center, and at least one lens of imaging optics 30 can be lowered below folding ring reflector 26 (as illustrated in FIG. 4) and even below refracting ring 24 (as illustrated in FIGS. 5 and 6).

Light beams 96 from oriented reflector ring 25 are not blocked by imaging optics 30.

Imaging optics 30 can be lowered such as to block first reflected light beams 92 (as illustrated in FIG. 5) and even block light beams 94.

The blocking can occur when the distance between area 42 and imaging optics 30 should be smaller than the distance between area 42 and folding ring reflector 26 or smaller than the distance between area 42 and refracting ring 24.

Imaging optics 30 may block the light in the mentioned above manner when uniform dark field illumination is required over a large field of view while maintaining a very small working distance (between area 42 and imaging optics 30).

Figure 6A:
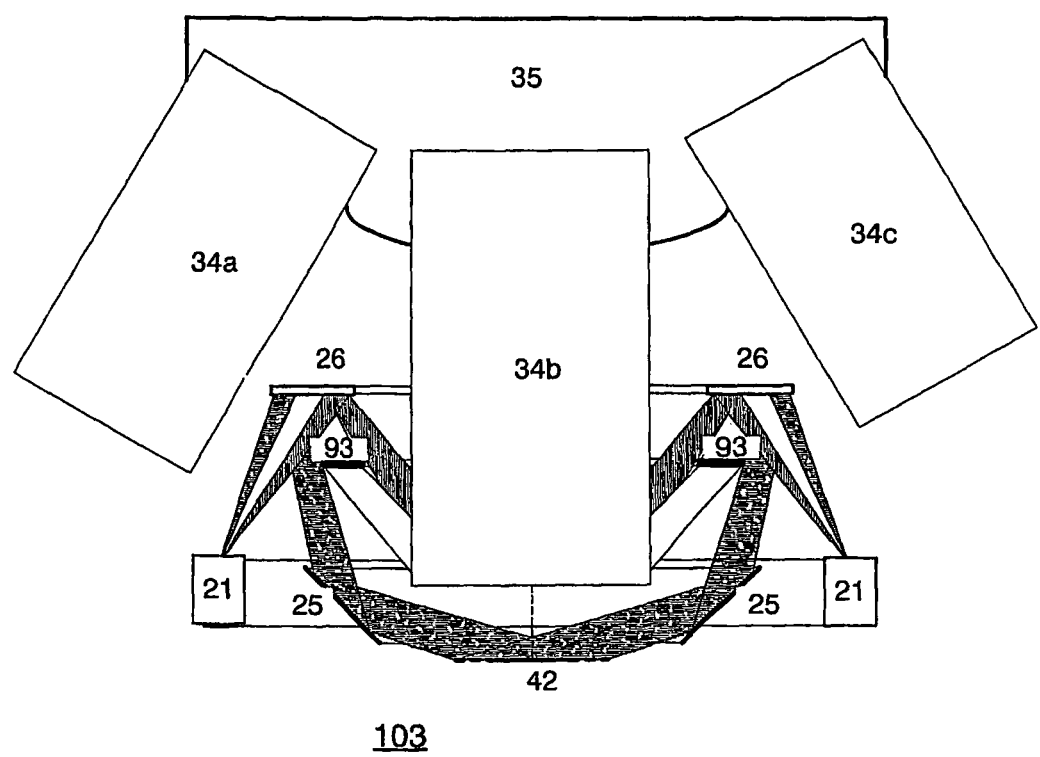
Figure 7A:
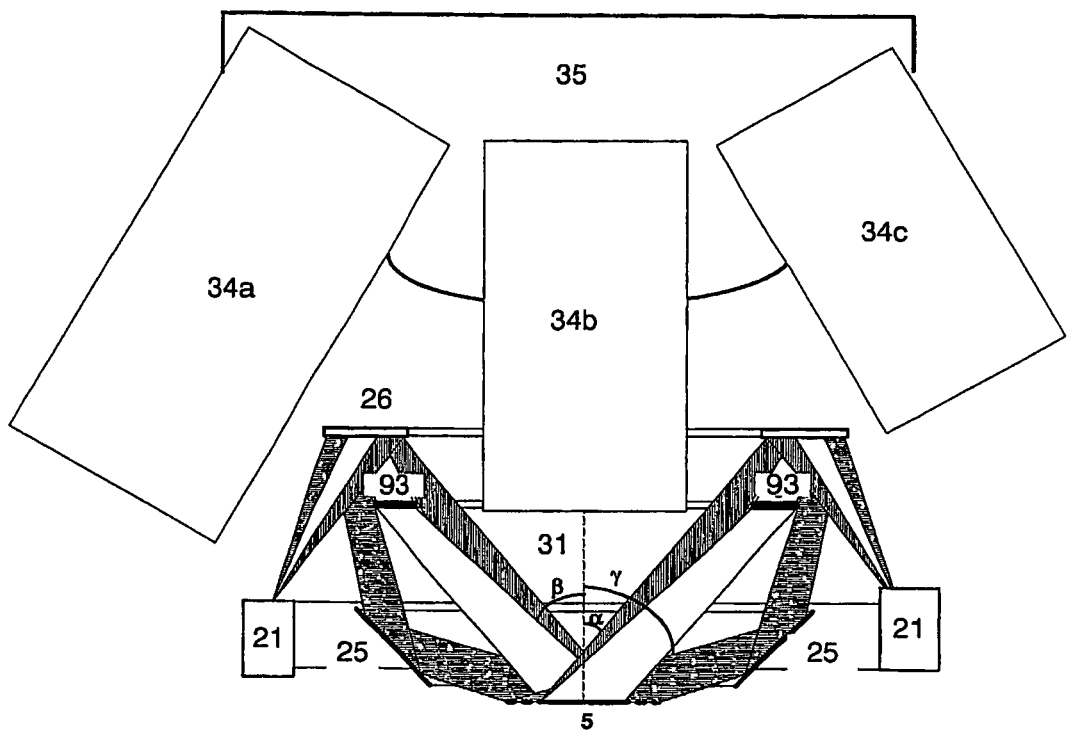

According to an embodiment of the invention the dark field inspection system 103 and especially its imaging optics 30 includes three different objective lenses 34a-34c that have three different magnification factors. These are illustrated in FIGS. 6A and 7A.

These three objective lenses are connected to a nosepiece 35 that can be lifted and rotated in order to select the required objective lens. Nosepiece 35 and objective lenses 34a-34c are lifted prior to the rotation and lowered after the rotation. The lowering of nosepiece 35 allows the required objective lens to be positioned at a working distance that is smaller than the distance between area 42 and folding ring reflector 26 (as illustrated in FIG. 7A) or is even smaller than the distance between area 42 and refracting ring 24 (as illustrated in FIG. 6A).

Nosepiece 35 can be motorized and objective lenses 34a-34c can be designed for relatively long working distance.

Figure 3B:
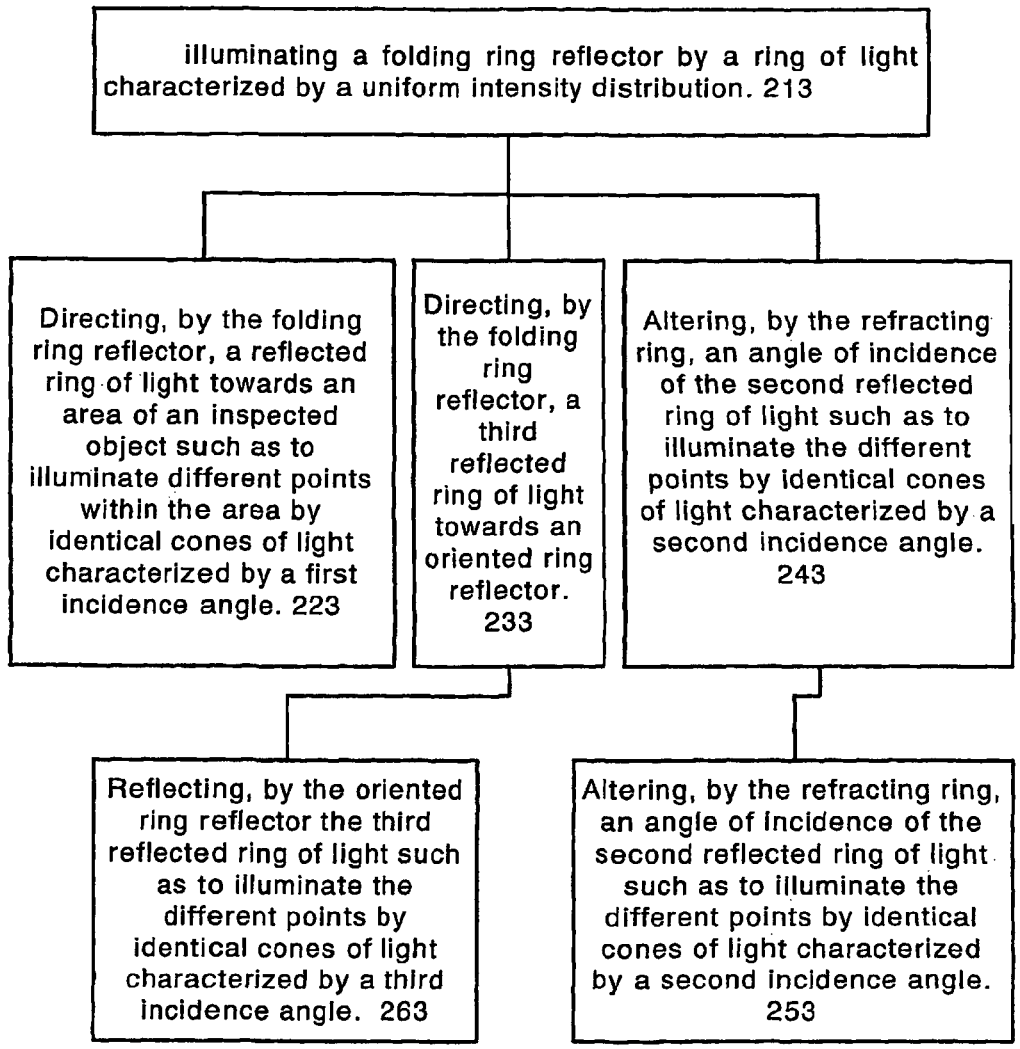

FIG. 3B is a flow chart of method 203 for dark field illumination, according to an embodiment of the invention.

Method 203 starts by stage 213 of illuminating a folding ring reflector by ring of light that is characterized by a uniform intensity distribution.

Stage 213 is followed by stage 223, 233 and 243.

Stage 223 includes directing, by the folding ring reflector, first reflected light beams towards an area of an inspected object such as to illuminate different points within the area by substantially identical cones of light having a first incidence angle. The first incidence angle can slightly deviate over the area. Thus, a point near the right end of the area can be illuminated by a slightly different cone of light that another point of the area that is located near the left end of the area.

Stage 233 includes directing, by the folding ring reflector, second reflected light beams towards a refracting ring.

Stage 243 includes directing, by the folding ring reflector, third reflected light beams towards an oriented ring reflector.

Stage 233 is followed by stage 263 of altering, by the refracting ring, an angle of incidence of the second reflected light beams such as to illuminate the different points by substantially identical cones of light having a second incidence angle. The second incidence angle can slightly deviate over the area.

Stage 243 is followed by stage 253 of reflecting, by the oriented ring reflector the third reflected light beams such as to illuminate the different points by substantially identical cones of light having a third incidence angle. The third incidence angle can slightly deviate over the area.

The ring reflector, the oriented ring reflector and the refracting ring are co-centric to an optical axis of a dark field illuminator that includes the light source, the folding ring reflector, the oriented ring reflector and the refracting ring. The folding ring reflector is positioned above the refracting ring and the light source.

Stages 223, 253 and 263 can be followed by generating detection signals in response to light omitted from area 42, processing the detection signals to locate defects, and the like.

According to various embodiments of the invention at least one of the following (or a combination thereof) occurs: (i) the first, second and third incidence angles do not overlap; (ii) the third incidence angle includes incidence angles that are proximate to ninety degrees; (iii) method 203 further includes directing, by the folding ring reflector, another reflected light beams towards another refracting ring and altering, by the other refracting ring, an angle of incidence of the second reflected light beams such as to illuminate the different points by substantially identical cones of light characterized by another incidence angle; (iv) each of the light source, the refracting ring and folding ring reflector has an opening through which at least one lens of an imaging optics can be placed; (v) each of the light source, the refracting ring and folding ring reflector has an opening through which at least one lens of an imaging optics can be placed such as to block at least the first reflected light beams; (vi) each of the light source, the refracting ring and folding ring reflector has an opening through which at least one lens of an imaging optics can be placed such as to block the first reflected light beams and light that is refracted by the refracting ring; (vii) the light source is a pulsed light source; and (viii) the light source is a continuous light source.

FIG. 3C illustrates illumination pattern 302, according to an embodiment of the invention.

Substantially each point of area 42 (such as arbitrary point 43) is illuminated by substantially the same illumination pattern—illumination pattern 302 that includes three cones 92, 94 and 96. Each cone is defined by a zenith angle, whereas the three zenith angles are referred to as alpha, betta and gamma respectively. The values of alpha, betta and gamma can slightly deviate across the whole illuminate area.

Over the whole illuminated area the incidence angles can slightly change.

Fourth Configuration

There are machine vision applications where the image characteristics are affected by the illumination angle of incidence. Thus, it is sometimes valuable to have the option to select the optimal angle of incidence for best image. Such a selection can be provided by dark field inspection system of FIG. 8A.

Figure 8A:
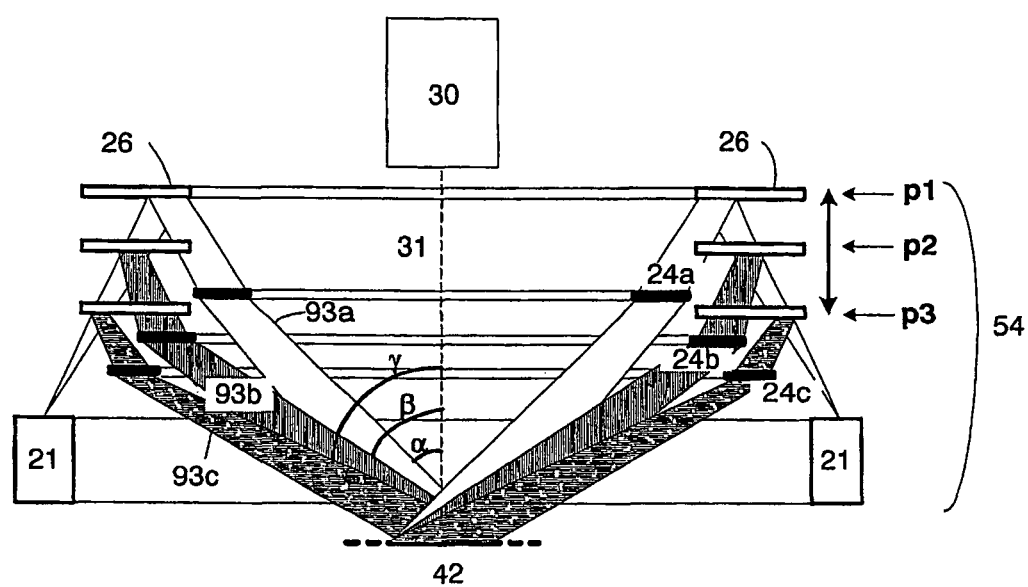

FIG. 8A is a cross sectional view of dark field inspection system 104 according to another embodiment of the invention.

Dark field inspection system 104 includes imaging optics 30 and dark field illuminator 54.

Dark field illuminator 54 includes: light source 21, folding ring reflector 26, multiple refracting rings 24a-24c and a reflector ring positioning unit that is not shown (for simplicity of explanation).

Light source 21 is adapted to provide a ring of light characterized by uniform intensity distribution. The ring of light is bounded by two co-centric cones that have the same imaginary base (defined by light source 21) but spaced apart apexes. The cross section of these beams (as illustrated in FIG. 8A) is a narrow fan.

The reflector ring positioning unit is adapted to position folding ring reflector 26 at a selected position out of multiple possible positions. FIG. 8A illustrates three possible positions (p1, p2 and p3) of folding ring reflector 26, although at any given point in time the folding ring reflector 26 is positioned only in one of these positions.

When folding ring reflector 26 is positioned in a selected position (p1, p2 or p3) it directs reflected light beams (93a, 93b or 93c) towards a selected refracting ring out of the multiple reflecting rings 24a-24c.

Each refracting ring alters an angle of incidence of the reflected light beams such as to illuminate different points within an area of an inspected object by substantially identical cones of light characterized by an incidence angle. Different refracting rings are associated with different incidence angles.

Folding ring reflector 26, each ring refractor (out of 24a-24c) and light source 21 are co-centric to the optical axis 31 of dark field illuminator 54.

Conveniently, each refracting ring is positioned above light source 21 and below folding ring reflector 26. This is not necessarily so. For example, light source 21 can be positioned above one or more refracting ring.

According to various embodiments of the invention at least one of the following (or a combination thereof) occurs: (i) different refracting rings are located at different heights and have different radiuses, (ii) the dark field inspection system further includes an imaging optics and at least one lens of the imaging optics is located within a space defined by the light source and by at least one refracting ring, (iii) the light source is a pulsed light source, and (iv) the light source is a continuous light source.

Figure 8B:
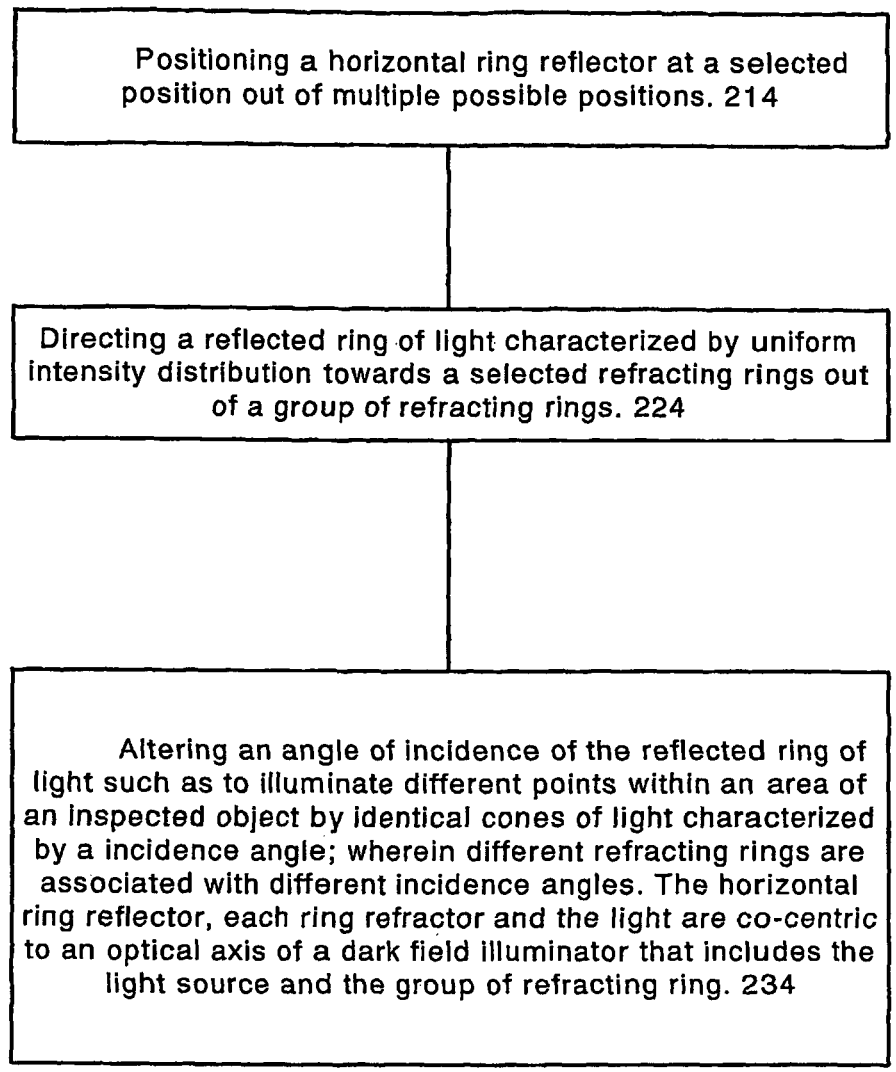

FIG. 8B is a flow chart of method 204 for dark field illumination, according to an embodiment of the invention.

Method 204 starts by stage 214 of positioning a folding ring reflector at a selected position out of multiple possible positions.

Stage 214 is followed by stage 224 of directing reflected ring of light characterized by uniform intensity distribution towards a selected refracting ring out of a group of refracting rings.

Stage 224 is followed by stage 234 altering an angle of incidence of the reflected light beams such as to illuminate different points within an area of an inspected object by identical (or substantially identical) cones of light characterized by a zenith angle; wherein different refracting rings are associated with different zenith angles. The folding ring reflector, each ring refractor and the light are co-centric to an optical axis of a dark field illuminator that includes the light source and the group of refracting ring.

Conveniently, different refracting rings are located at different heights and have different radiuses.

Conveniently, at least one lens of the imaging optics is located within a space defined by the light source and by at least one refracting ring.

According to various embodiments of the invention a bright field illuminator is provided in addition to the dark field illuminator. Typically one illuminator is activated at a given point of time but this is not necessarily so.

Although the invention has been described in conjunction with specific embodiments thereof, it is evident that many alternatives, modifications and variations will be apparent to those skilled in the art, accordingly, it is intended to embrace all such alternatives, modifications and variations that fall within the spirit and broad scope of the appended claims.

What is claimed is:

1. A dark field illuminator, comprising:
a light source adapted to provide ring of light characterized by uniform intensity distribution;
a folding ring reflector adapted to receive the ring of light and to: direct first reflected light beams towards an area of an inspected object, direct second reflected light beams towards a refracting ring, and direct third reflected light beams towards an oriented ring reflector;
wherein the first reflected light beams illuminate different points within the area of the inspected object by substantially identical cones of light characterized by a first incidence angle;
wherein the refracting ring alters an angle of incidence of the second reflected light beams such as to illuminate the different points within the area of the inspected object by substantially identical cones of light characterized by a second incidence angle;
wherein the oriented ring reflector reflects the third reflected light beams such as to illuminate the different points within the area of the inspected object by substantially identical cones of light characterized by a third incidence angle;

wherein the folding ring reflector, the oriented ring reflector and the refracting ring are co-centric to an optical axis of the dark field illuminator.

2. The dark field illuminator according to claim 1 wherein the first, second and third incidence angles do not overlap.

3. The dark field illuminator according to claim 1 wherein the third incidence angle is proximate to ninety degrees.

4. The dark field illuminator according to claim 1 further comprising at least one other refracting ring, each other refracting ring being positioned such as to receive a portion of reflected light beams and refract them such as to illuminate the different points by substantially identical cones of light characterized by another incidence angle.

5. The dark field illuminator according to claim 1 wherein each of the light source, the refracting ring and folding ring reflector has an opening through which at least one lens of an imaging optics can be placed.

6. The dark field illuminator according to claim 1 wherein each of the light source, the refracting ring and folding ring reflector has an opening through which at least one lens of an imaging optics can be placed such as to block the first reflected light beams.

7. The dark field illuminator according to claim 1 wherein each of the light source, the refracting ring and folding ring reflector has an opening through which at least one lens of an imaging optics can be placed such as to block the first reflected light beams and light beams that are refracted by the refracting ring.

8. The dark field illuminator according to claim 1 wherein the light source is a pulsed light source.

9. The dark field illuminator according to claim 1 wherein the light source is a continuous light source.

10. The dark field illuminator according to claim 1, wherein the light source, the refracting ring and the oriented ring reflector are positioned below the folding ring reflector.

11. The dark field illuminator according to claim 10, wherein the light source is positioned between the refracting ring and the oriented ring reflector.

12. The dark field illuminator according to claim 10, wherein the light source is positioned below the refracting ring.

13. A dark field illumination method, comprising:
illuminating a folding ring reflector by ring of light characterized by a uniform intensity distribution;
directing, by the folding ring reflector, first reflected light beams towards an area of an inspected object such that different points within the area of the inspected object are illuminated by substantially identical cones of light characterized by a first incidence angle;
directing, by the folding ring reflector, second reflected light beams towards a refracting ring;
directing, by the folding ring reflector, third reflected light beams towards an oriented ring reflector;
altering, by the refracting ring, an angle of incidence of the second reflected light beams so as to illuminate the different points within the area of the inspected object by substantially identical cones of light characterized by a second incidence angle; and
reflecting, by the oriented ring reflector the third reflected light beams so as to illuminate the different points within the area of the inspected object by substantially identical cones of light characterized by a third incidence angle;
wherein the ring reflector, the oriented ring reflector and the refracting ring are co-centric to an optical axis of a dark field illuminator that comprises the light source, the folding ring reflector, the oriented ring reflector and the refracting ring.

14. The dark field illumination method according to claim 13 wherein the first, second and third incidence angles do not overlap.

15. The dark field illumination method according to claim 13 wherein the third incidence angle is proximate to ninety degrees.

16. The dark field illumination method according to claim 13 further comprising: directing, by the folding ring reflector, another reflected light beams towards another refracting ring; and altering, by the other refracting ring, an angle of incidence of the second reflected light beams such as to illuminate the different points by substantially identical cones of light characterized by another incidence angle.

17. The dark field illumination method according to claim 13 wherein each of the light source, the refracting ring and folding ring reflector has an opening through which at least one lens of an imaging optics can be placed.

18. The dark field illumination method according to claim 13 further comprising lowering the imaging optics through an opening defined by each of the light source, the refracting ring and folding ring reflector, such as to block at least the first reflected light beams.

19. The dark field illumination method according to claim 13 further comprising lowering the imaging optics through an opening defined by each of the light source, the refracting ring and folding ring reflector, such as to block the first reflected light beams and light that is refracted by the refracting ring.

20. The dark field illumination method according to claim 13 comprising providing pulsed ring of light.

21. The dark field illumination method according to claim 13 comprising providing continuous ring of light.

22. The dark field illumination method according to claim 13, wherein the light source, the refracting ring and the oriented ring reflector are positioned below the folding ring reflector.

23. The dark field illumination method according to claim 22, wherein the light source is positioned between the refracting ring and the oriented ring reflector.

24. The dark field illumination method according to claim 22, wherein the light source is positioned below the refracting ring.

* * * * *